United States Patent [19]

Neufeld

[11] 4,381,770

[45] May 3, 1983

[54] METHOD AND APPARATUS FOR PERFORMING PERCUTANEOUS BONE SURGERY AND NEW PIN IMPLANT

[76] Inventor: Alonzo J. Neufeld, 1650 N. Parway Dr., Glendale, Calif. 91206

[21] Appl. No.: 315,238

[22] Filed: Oct. 26, 1981

[51] Int. Cl.³ .......................... A61F 5/04; A61B 17/18
[52] U.S. Cl. .......................... 128/92 BA; 128/92 EB; 128/92 A
[58] Field of Search ............ 128/92 BA, 92 BB, 92 B, 128/92 E, 92 EA, 92 EB, 92 A, 92 R, 83

[56] References Cited

U.S. PATENT DOCUMENTS

| | | | |
|---|---|---|---|
| 2,486,136 | 10/1949 | Ericsson | 128/92 BA |
| 2,536,296 | 1/1951 | Longfellow | 128/92 BA |
| 3,892,232 | 7/1975 | Neufeld | 128/92 EB |
| 4,009,712 | 3/1977 | Burnstein et al. | 128/92 BA |
| 4,040,129 | 8/1977 | Steinemann et al. | 128/92 BA |
| 4,263,903 | 4/1981 | Griggs | 128/92 E X |

FOREIGN PATENT DOCUMENTS 2406430  6/1979  France ............................. 128/92 BB

OTHER PUBLICATIONS

Intertrochanteric Fractures, The Journal of Bone & Joint Surgery, Jan. 1944, vol. 26, No. 1, pp. 54,55 & 61. "Internal Fixation for Intertrochanteric Fractures" by G. M. Taylor et al., The Journal of Bone & Joint Surgery, Oct. 1944, vol. 26, No. 4, pp. 707-712.

Primary Examiner—Ronald L. Frinks
Attorney, Agent, or Firm—Harlan P. Huebner

[57] ABSTRACT

Apparatus and method of performing percutaneous bone surgery particularly to repair a particular fractured trochanteric portion of a femur. The technique includes the making of a small first incision to the bone, introducing a tubular guide, placing a drill in the tube activating the same, drilling a bore into the bone, withdrawing the drill and guide and inserting a new pin and pin insertion means to place the pin in position in the bore and due to its design leaving a portion extending from said bone bore to abut and lie against the femur at approximately 145° to the angle of the portion of the pin in the bore. In addition the pin insertion means includes a portion adapted to abut the exterior skin and serve as a guide for an additional small incision, insertion of a tubular guide, placing a drill in the guide, drilling a second bore below the first bore and at an angle thereto. The pin includes a bore which is aligned with the tubular guide when in its second position and is adapted to receive a fastening means to lock the pin to the bone during the bone healing process.

10 Claims, 10 Drawing Figures

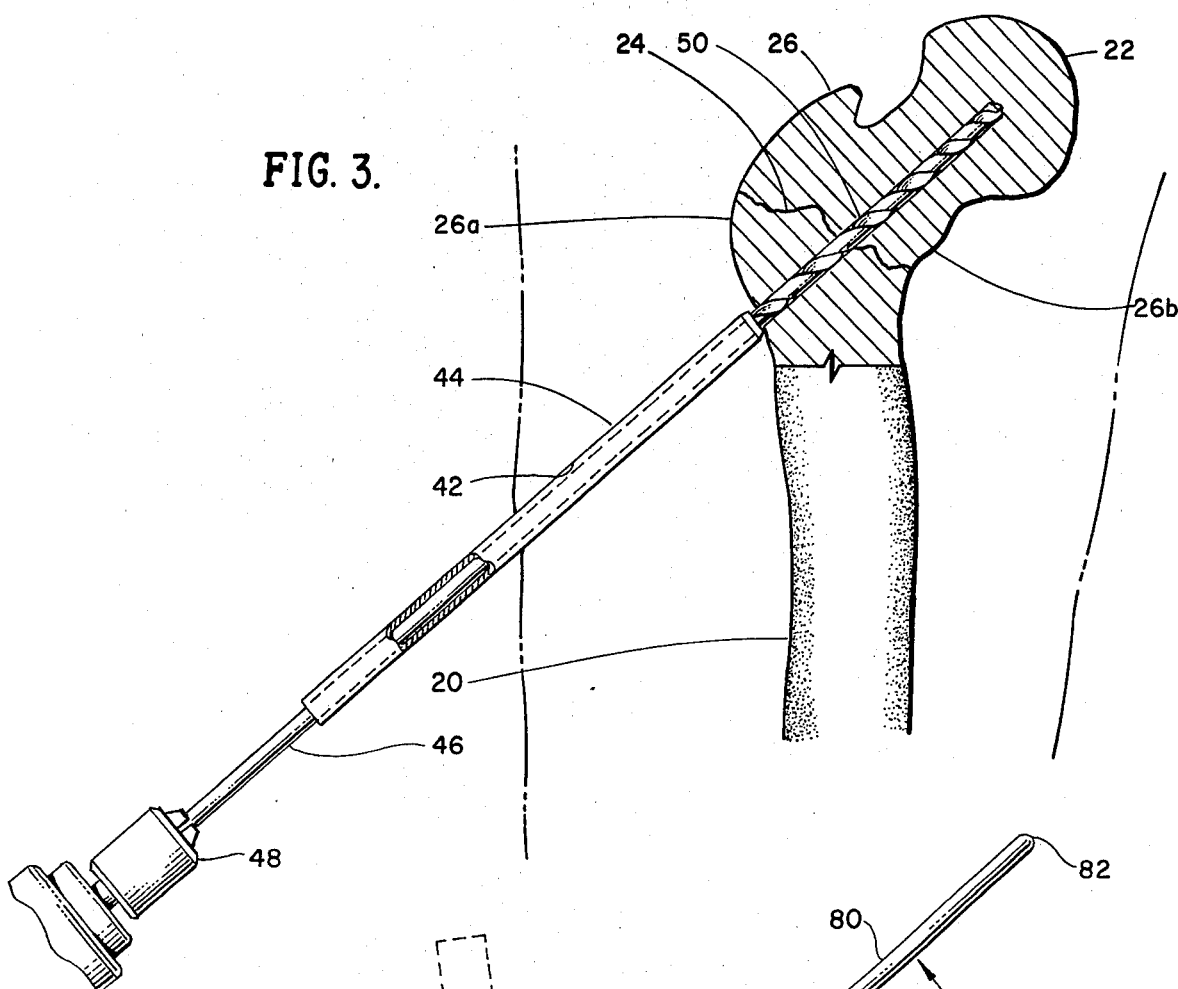
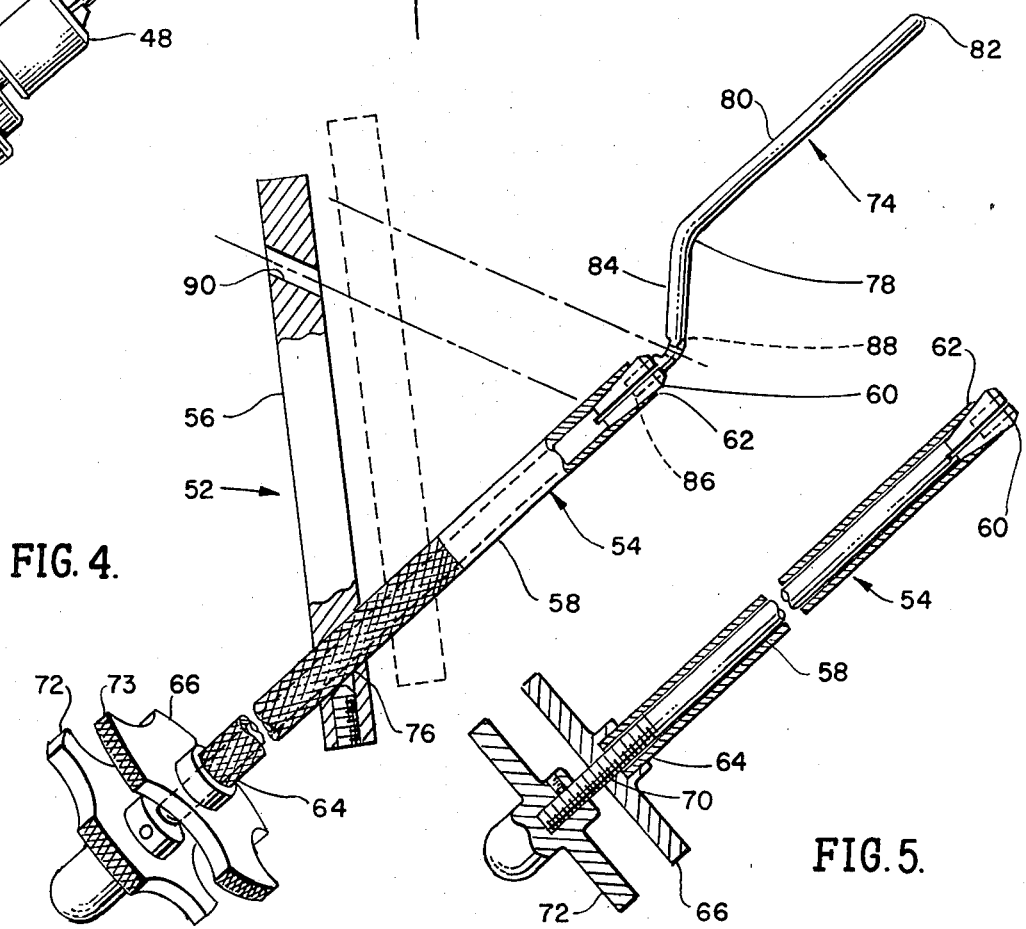

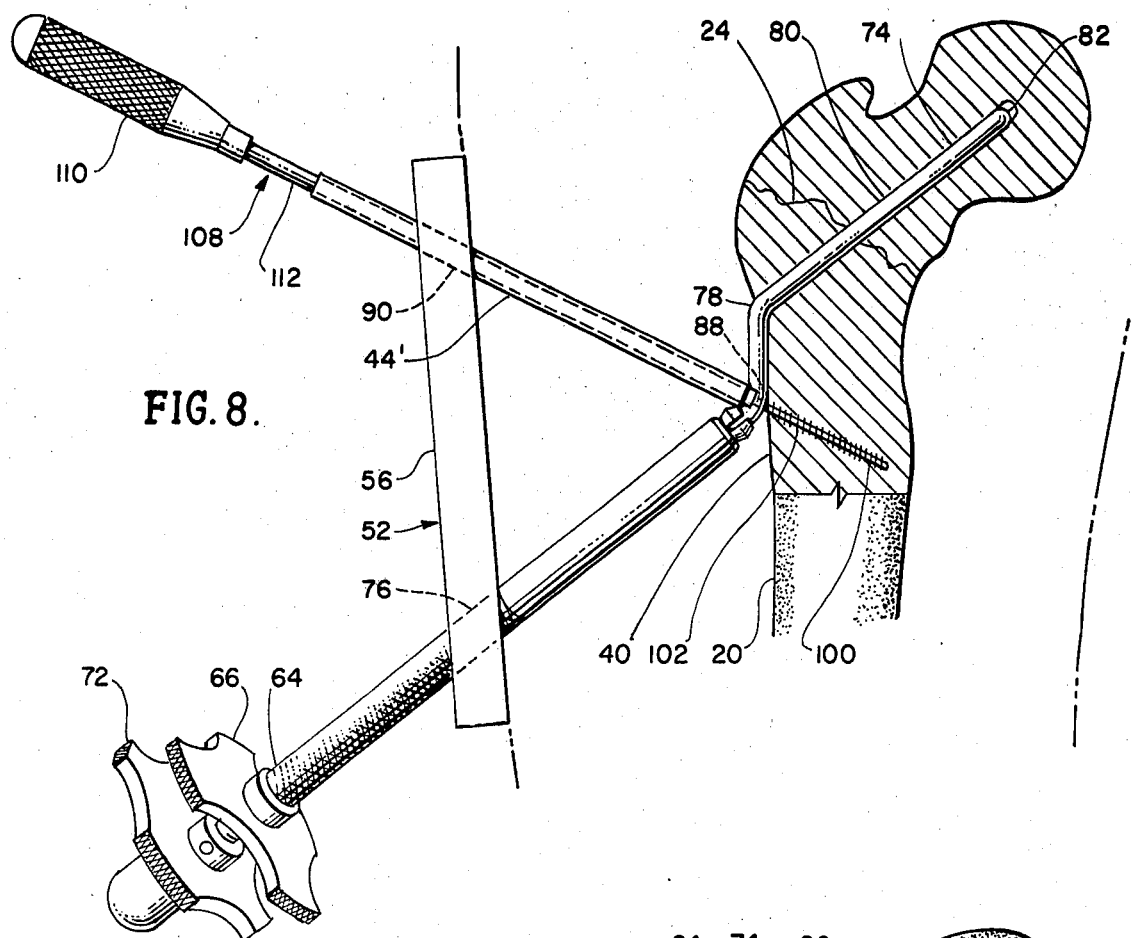
FIG. 8.
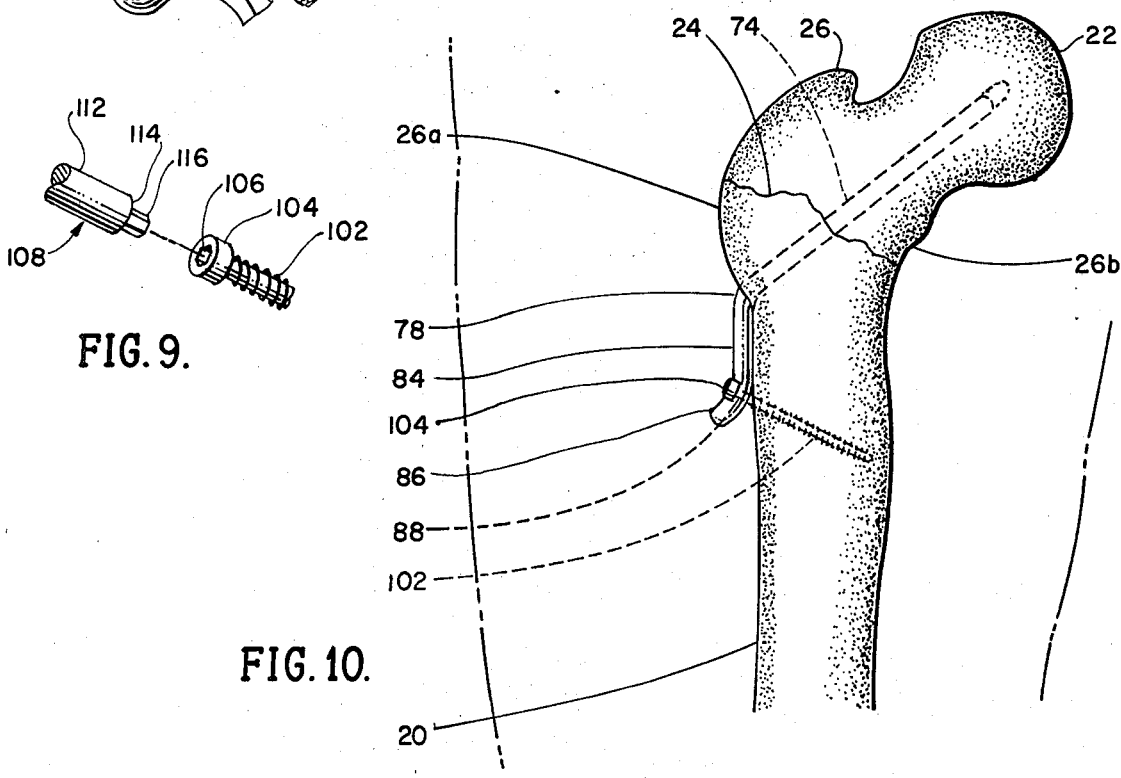
FIG. 9.
FIG. 10.

METHOD AND APPARATUS FOR PERFORMING PERCUTANEOUS BONE SURGERY AND NEW PIN IMPLANT

BACKGROUND OF THE INVENTION

The use of metal pins or other implants to immobilize and support fractured bone sections while they heal, or for permanent use are well known. These implants are particularly useful for fractures of the upper ball joint of the femur. Improvements in this art as directed to relatively straight pins and the technique used therewith is shown and claimed in my U.S. Pat. No. 3,892,232, issued July 1, 1975.

However, while the above patent is useful for the majority of relatively simple femur ball joint breaks, the need for both new implants and the technique to insert the same is required for more complex breaks. As an illustration with certain bone deterioration or fractures the ball joint of the femur may have a break across the heel or angle of the joint. In addition, the weight of the patent can be of such proportion to exert greater downward pressure on the joint and special fracture and without an adequate pin implant prevent healing.

My improvement setforth in the present application covers both a new type of pin implant as well as apparatus and the technique to accomplish bone surgery.

SUMMARY OF THE INVENTION

The present invention involves a departure from the use of mere straight implant pins, as in my previous patent. The new pin is constructed in such a way as to include an angled portion to the part inserted within the bone and an extension thereto for securement to the bone. In addition, I have developed various pieces of new equipment to use for positioning and securing the pin in place.

In general tubular guides are utilized at angles one to the other to assure the guidance and insertion of tools through the small stab wounds in the skin to place the implant pin in position and fix it to the bone.

In addition to the tubular guides I provide new insert holders and an exterior guide bar for aligning the tubes.

A number of features contributing to the efficiency of the apparatus, technique and the method will be discussed in the subsequent detailed description.

BRIEF DESCRIPTION OF THE DRAWINGS

FIG. 3, illustrates the drilling procedure in the femur ball joint;

FIG. 4, illustrates additional apparatus and my new implant pin being positioned for insertion;

FIG. 5, is a cross sectional view of a new insertion tool of FIG. 4;

FIG. 8, is a view like FIG. 7 but with a fastener and wrench in position to affix the new pin to the bone;

FIG. 9, is a detailed view of the fastener head end driver; and

FIG. 10, shows the new implant pin in position and all the apparatus to insert and fix the same removed.

DESCRIPTION OF THE PREFERRED EMBODIMENT

Figure 1:
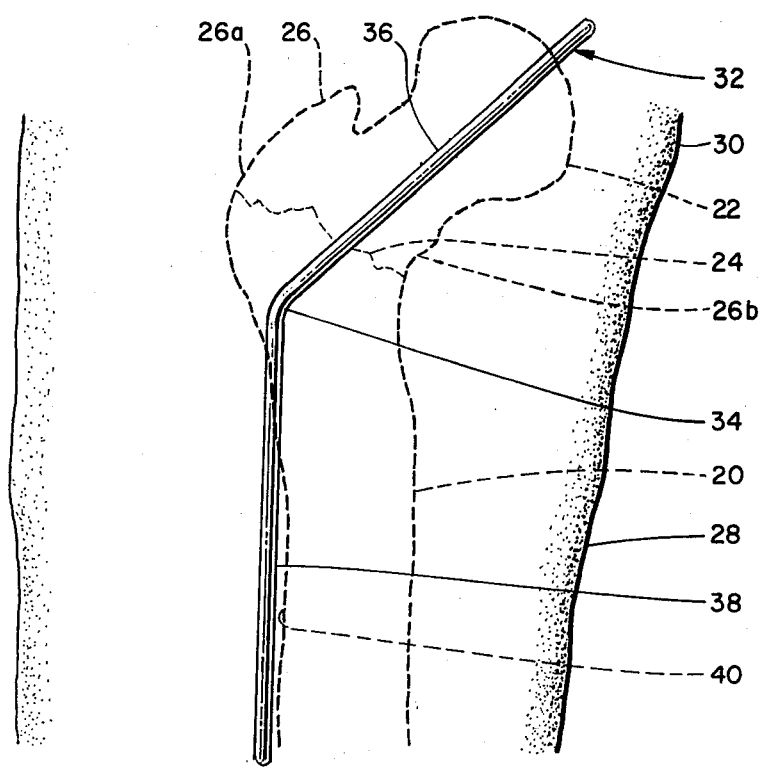
FIG. 1, is a view of a femur bone and upper ball joint with a guide pin placed on the exterior of the skin.
Figure 2:
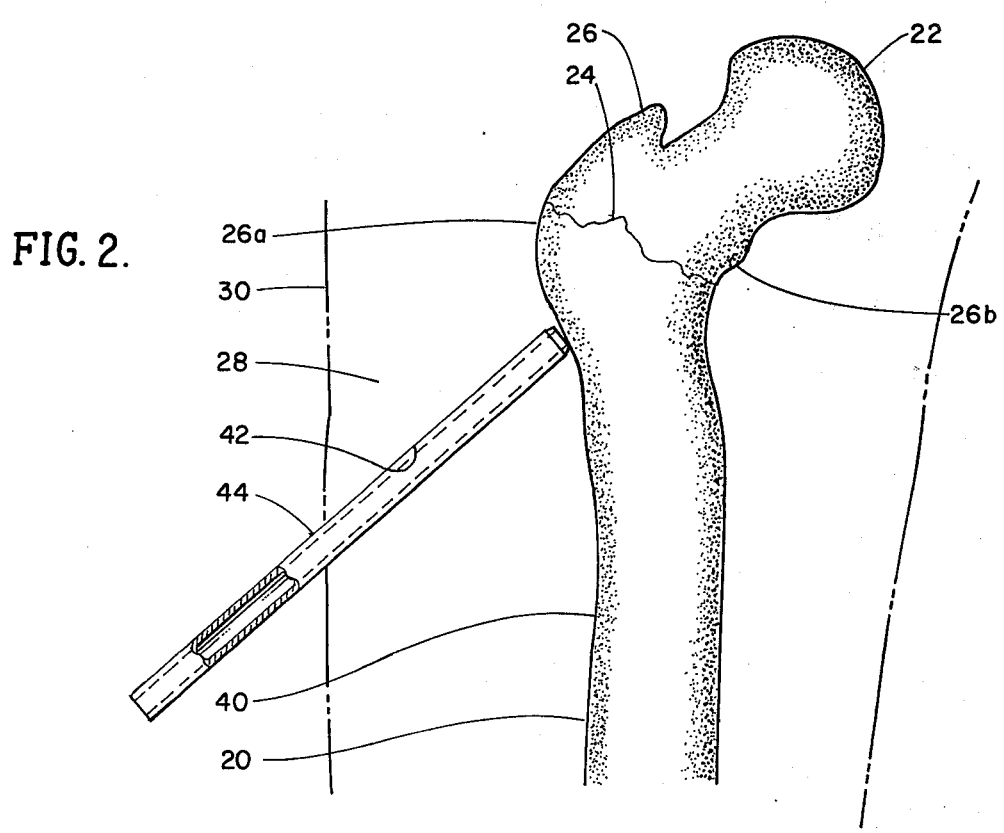
FIG. 2, is a view of a first tubular guide and initial stage of the technique.

For purposes of illustration there is shown a femur bone 20 wherein the upper ball joint 22 there is a fracture represented by irregular line 24. This particular fracture 24 is different than those in the head portion or fovea capitis femoris 22. This break, as can be seen occur across the bone 20 below the trochanter major 26 from the outer heel 26a to the trochanter minor 26b. It can be said to be across the "neck portion" of the ball 22. Surrounding the bone 20 is leg body tissue 28 encased in skin 30.

In order to commence the surgery, a guide pin 32 is laid on top of the skin 30 and aligned with the femur 20 and upper joint 22 as shown. The guide pin 32 is an elongated rod which is circular in cross section. The rod is bent at 34 so that there is an upper femur upper joint guide portion 36 and at an angle thereto a lower femur guide portion 38. The angle at the bend is preferably 145°.

The positioning of the pin 32 is done with the aid of a conventional fluoroscope (not shown). The object is to move the pin 32 around so the upper joint guide portion 36 will besect the fracture 24 and also so that the lower portion 38 lies parallel with and adjacent the exterior surface 40 of the femur 20. FIG. 1 illustrates the correct positioning so that two planes or angles are achieved; first the angle of the upper joint of the femur 20 to cross the fracture 24 and secondly to establish the angle and position of the exterior surface 40 of the femur.

With the angle created by the portion 36 arrived at, the next step is to make a small incision 42 from the exterior skin 30 through the tissue 28 to the bone 20 on the appropriate angle of the guide upper portion 36. An elongated tubular guide 44 is introduced through the incision 42. It is preferable that the tube be in 6" increments so that it will enable the surgeon to select a drill 46 of proper length.

Next, as is evident from FIG. 3, the drill 46, attached to a conventional chuck 48 and rotatable by a power source not shown is inserted into the tubular guide 44 and when it hits the joint 22, the joint of the femur 20 is drilled, such as seen in FIG. 3. The drill 46 is withdrawn leaving a bore 50, generally drilled approximately ¼" longer than the pin to be inserted for the fracture fragments to be able to compact.

At this point, the ball or bone joint 22 is ready for a pin to be inserted to aid in the healing of the fracture 24. In order to accomplish this the tubular guide 44 is withdrawn from the incision 42 so as to accommodate a portion of the pin insertion means generally designated 52. The insertion means 52 is best seen in FIGS. 4 and 5.

The pin insertion means 52 includes an elongated pin gripping means 54 and adjustable linking means or guide leg brace 56. The pin gripping means 54 preferably has a tube 58 with a convention form of pinch chuck 60 mounted in one end 62 of the tube 58. At the other end 64 a fixed handle 66 is attached thereto. Threadable inserted through handle 66 and within the tube 58 is a threaded shaft 70. Secured to the shaft 70 is a second handle 72. The exterior perimeter shape of the handles 66 and 72 is immaterial, but should include positive gripping portions 73. In operation, a pin generally designated 74 has an end inserted in the chuck 60. To maintain the pin 74 in place the handle 72 is rotated forcing the tube 58 forward so as to squeeze the chuck elements together and lock the pin 74 in place.

The selection of the pin 74 of proper length can be accomplished in several ways not the least of which is to establish the linear dimension such as shown and claimed in my U.S. Pat. No. 3,892,232.

Associated with the gripping means 54 is the adjustable linking means or guide leg brace 56. The brace 56 is preferably an elongated metal bar generally square in cross section. Adjacent one end a bore 76 is cut through the brace 56 at a 45° angle to the elongated plane of the brace 56. The gripping tube 58 is of a diameter generally complimentary with the bore 76 so the brace 56 can be moved along the tube 58.

The pin 74 is of a very unique design and shape to be utilized with the particular fracture 24. As can be seen from the drawings the pin 74 is preferably of a uniform circular diameter throughout. The pin 74 is bent at 78 to form a forward straight portion 80 with a rounded forward end 82. This portion 80 is adapted to be inserted in the bore 50 cut into the femur ball joint 22.

The pin 74 at bend 78 includes a short rear extension 84 which has an axis approximately 145° to the axis of the portion 80. Located in the outwardly bend end 86 is a bore 88. The axis of the bore 88 is at an opposite 45° angle relative to the axis of the short extension 84. The purpose of the bore 88 will be subsequently described. The extension 84 may have threads whereby it may be gripped for withdrawal of pin 74 or it may be smooth for insertion in a chuck.

Once the pin 74 is gripped by the insertion means 54, see FIG. 4, it is really for proper insertion. By aid of the small incision 42 and a fluoroscope, the pin 74 is inserted through the incision and into the bore 50 in the bone as can be seen the bore is longer than the inserted portion of the pin 74.

As can also be seen, proper insertion of the pin 74 requires the forward straight portion 80 to be inserted in the drilled bore 50 with the short rear extension 84 abutting the exterior 40 of the femur bone 20. Once the pin 74 is inserted, FIG. 4, the guide leg brace 56 is moved inward to abut against the skin 30 of the leg. In this way two things are accomplished, one the pin 74 and insertion means 54 are stabilized and, two the access to the bore 88 of the pin is assured.

Figure 6:
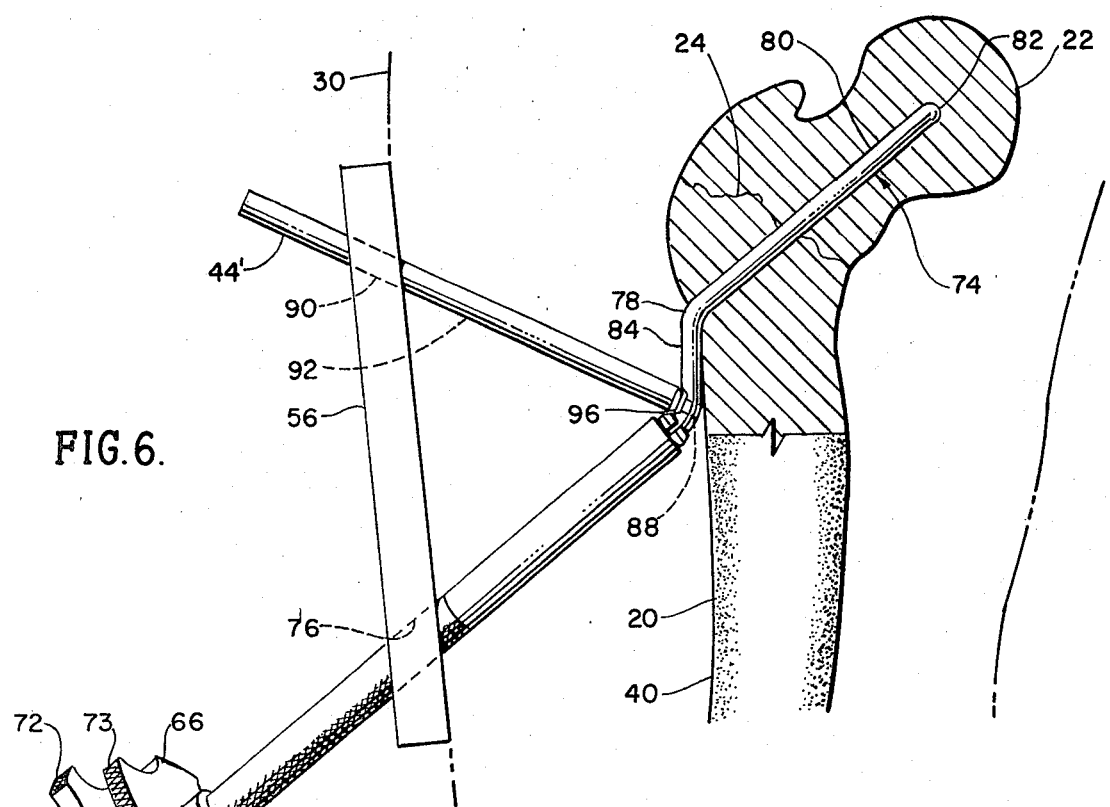
FIG. 6, is a view similar to FIG. 4 but with a tubular guide in another position and the new pin insertion in the bone.
Figure 7:
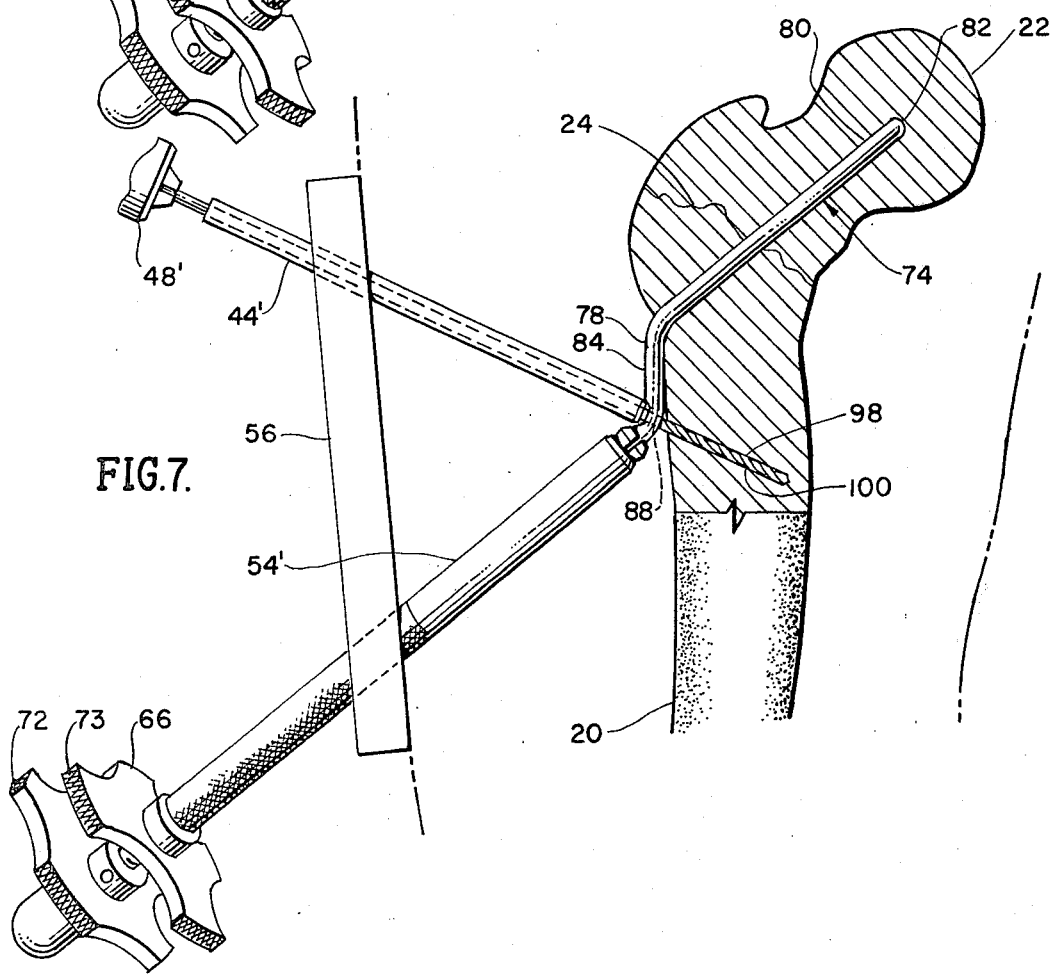
FIG. 7, is a view similar to FIG. 6 with a drill inserted in the tubular guide to drill an additional bore in the bone below the upper joint of the femur.

As can be seen in FIG. 6 the linking means or guide leg brace 56 also includes a second bore 90 at a 45° angle to the axis of the bar 56. A projection of the bore 90 would intersect a projection of the bore 76 forming an isosceles triangle. The base of the triangle (the bar 56) depending on the thickness of the leg can vary in position, see FIG. 4, possibly making an equalateral triangle, but in any event always an isosceles triangle with two sides being equal. The apex of the means 54 and guide 44' always end at the bore 88.

With bar 56 in abutting position another small incision 92 is made through the skin 30 and tissue 28 directly to the bore 88 of the pin 74. The same guide tube 44' or a second tube is then inserted through the guide bore 90 of the bar 56 and the incision 92. Because of the predetermined angle of guide bore 90 the end 96 of the tube 44' which is slightly beveled, will be exactly aligned with the bore 88 in pin 74, see FIG. 6.

With the guide 44' in position, a conventional drill bit 98 is secured to chuck 48' and is inserted through the guide tube 44' and bore 88 to drill bore 100 in the femur bone 20. The drill 98 is normally of a lesser diameter than the drill 46 for reasons which will become apparent.

The next step is to withdraw the drill 98 from the prepared bore 100 and to insert a fastening means or screw 102. Preferably the screw 102 has a head 104 with a tool interlock means or an Allen socket 106 to receive a driver means 108. The driver 108 includes a handle 110, shank 112 and at the end 114 of the shank includes a head extension 116 of a perimeter dimension comparable with Allen socket 106.

By rotating the handle 110 the screw 102 is set through the bore 88 of pin 74 into the bone to fix the pin 74 in position.

As can be seen from the final figure of the drawings, FIG. 10, the pin 74 is set into position and utilizes the screw 102 to support the downward weight on the joint and in turn the pin 74. It has been found that in the case of unique fractures such as shown at 24 this new pin 74 and the technique of inserting the same has proven highly effective.

Further, with the pin 74 and the fastening thereof manner described there is increased strength with the extention 84 biased to the femur 20 by means of the screw 102. Without this new invention, particular fractures 24 when conventional pins are used have a tendency to "slide" because the body weight exerts downward pressure preventing true healing of the fracture. By the tying of the pin 74 to the femur 20 "sliding" is prevented and as long as the femur 20 holds up it absorbs the weight maintaining the pin forward portion 80 stable.

Although I have described my invention in what I have conveived to be the preferred embodiments, it is recognized that departures may be made therefrom with the scope of my invention.

I claim:

1. For performing percutaneous bone surgery and aid the healing of a fracture, an elongated tubular guide adapted to be inserted through a small skin surface and tissue incision and positioned at a predetermined angle to the axis of the femur bone with an end abutting said bone and its exterior end remaining outwardly of said skin surface, said guide serving to direct a drill bit to said bone and assuring proper angular direction to form a first bore in said bone when said drill bit is activated, the combination of:
 a pin means having one forward straight portion with a first axis for insertion in said first bore and a second short rear extension portion having a second axis approximately 145° to said first axis, and a bore extending through said second short rear extension portion;
 a pin insertion means including pin gripping means to releasably hold said pin wherein said pin insertion means has a portion for entering said incision to place said forward straight portion by friction in said bore whereby said short rear extension is adapted to abut and be parallel to said femur leg bone;
 a second tubular guide for inserting through a small skin surface and tissue second incision above said first incision and at an angle thereto aligned with and abutting said bore in said pin;
 adjustable linking means securing said pin insertion means and said second tubular guide in a predetermined angular relationship;

said second tubular guide serving to direct a second drill bit through said bore to form a second bore in said bone when said drill bit is activated;

a fastening means with a tool interlock means at a rearward end inserted in said second bore to secure said pin to said femur; and a tool having a complimentary interlock means with said fastening means slidably inserted into said second guide to engage said fastening means.

2. The combination of claim 1 in which the tool interlock means on said fastening means is an Allen socket, and the complimentary interlock means on the tool is an extension of a configuration to interfit the Allen socket, so that rotation of the tool will rotate the fastening means.

3. The combination of claim 2 wherein the fastening means is a screw that is threadably rotated into said second bore to lock said pin in position.

4. The combination of claim 1 in which the adjustable linking means is an elongated guide leg brace having an axis and a first bore extending therethrough at an angle to said axis and a second bore remote from said first bore extending therethrough at an angle opposite to the angle of said first bore, wherein a projection of the bores would intersect outwardly of said brace.

5. The combination of claim 1 wherein the angle of each bone bore is 45° to the axis of said elongated leg brace.

6. The combination of claim 4 wherein said pin insertion means is slidably mounted through said first bore of said brace whereby said linking means may be moved to bear against the skin for stability.

7. The combination of claim 1 wherein said pin insertion means includes an elongated tube with a pinch chuck at one end adapted to releasably hold said pin for insertion into said first bore, a handle means remote said chuck and linked thereto to activate said chuck to clamp said pin or release the same.

8. The combination of claim 1 wherein said pin means has a uniform smooth diameter throughout its length, and being bent to form a forward straight portion having said first elongated axis and of a length slightly less than the length of said first bore in said bone, and a short rear extension extending at a 145° angle to the first elongated axis and a bore extending through said pin adjacent the end of said short rear extension.

9. In bone surgery for the implanting of a percutaneous pin therein by making of an incision of small diameter through skin and tissue to the surface of a femur bone, inserting a tubular guide through the incision, introducing a drill bit through the guide and activating said bit to drill a first bore in the bone and removing said drill comprising the new steps of:

removing said tubular guide;

selecting a pin of a length wherein a part thereof may be frictionally accommodated in said first bore and a second part is adapted to abut said femur and includes a bore therethrough;

utilizing a pin insertion means to releasably hold said pin;

inserting said pin and a portion of said pin insertion means through said incision so that a portion of said pin extends into said first bore;

adjusting a portion of said pin insertion means exterior to said skin to abut said skin for stability and another angular predetermination;

making a second incision above said first incision and at an angle thereto;

introducing a tubular guide into said incision to the surface of said pin and aligned with said bore in said second part of said pin;

introducing a drill bit through said guide and said bore to said bone and activating said bit to drill a second bore at a 45° angle to said first bore;

removing said drill;

inserting a fastening means into said tubular guide;

applying a tool to said fastening means and securing said pin to said bone; and removing said tubular guide.

10. A method as defined in claim 9 in which the adjusting of a portion of said pin insertion means exterior of said skin includes moving a leg guide brace inward or outward to abut the skin, and said tubular guide is introduced through a bore in said leg guide brace, said bore being at a 45° angle to the plane of said leg guide brace.

* * * * *